US012746377B2

(12) United States Patent
Browd et al.

(10) Patent No.: US 12,746,377 B2
(45) Date of Patent: Sep. 29, 2026

(54) DYNAMICALLY CONTROLLED CEREBROSPINAL FLUID SHUNT

(71) Applicant: Oaya, Inc., Seattle, WA (US)

(72) Inventors: Samuel Robert Browd, Mercer Island, WA (US); Ryan J. Douglas, Seattle, WA (US); Aaron Olafur Laurence Philippsen, Victoria (CA); Mark Drlik, Victoria (CA)

(73) Assignee: Oaya, Inc., Seattle, WA (US)

( * ) Notice: Subject to any disclaimer, the term of this patent is extended or adjusted under 35 U.S.C. 154(b) by 321 days.

(21) Appl. No.: 18/313,249

(22) Filed: May 5, 2023

(65) Prior Publication Data

US 2023/0355937 A1 Nov. 9, 2023

Related U.S. Application Data

(60) Provisional application No. 63/488,412, filed on Mar. 3, 2023, provisional application No. 63/477,158, filed
(Continued)

(51) Int. Cl.
*A61M 27/00* (2006.01)

(52) U.S. Cl.
CPC ... *A61M 27/006* (2013.01); *A61M 2202/0464* (2013.01); *A61M 2205/3331* (2013.01)

(58) Field of Classification Search
CPC ................. A61B 5/0215; A61B 5/031; A61M 2025/0003; A61M 27/006; A61M 39/28; A61F 2202/0464; A61F 2202/3331
See application file for complete search history.

(56) References Cited

U.S. PATENT DOCUMENTS

| | | | | |
|---|---|---|---|---|
| 6,432,050 | B1 | 8/2002 | Porat et al. | |
| 6,533,733 | B1 * | 3/2003 | Ericson | A61M 27/006 600/128 |

(Continued)

FOREIGN PATENT DOCUMENTS

| | | | |
|---|---|---|---|
| CN | 110575573 | A | 12/2019 |
| ES | 2694698 | A1 | 12/2018 |

(Continued)

OTHER PUBLICATIONS

Gonzalez, M., Implantable Systems for Continuous Liquorpheresis and CSF Replacement, Feb. 10, 2017, 10 pages.

(Continued)

*Primary Examiner* — Michele Kidwell
(74) *Attorney, Agent, or Firm* — Athorus, PLLC

(57) ABSTRACT

Apparatus and associated methods relate to smart shunt systems. In an illustrative example, a cerebrospinal fluid (CSF) shunt system includes an interface module and conduit(s) configured to provide selective fluid communication between a brain ventricle(s) and at least one reservoir. The interface module may be operably coupled to one or more control module(s). The control module(s) may, for example, be operably coupled to one or more actuator(s) and/or sensor(s) (e.g., in the interface module(s), external to the interface module(s)). The control module(s) may, for example, selectively operate one or more of the actuator(s) as a function of input received from one or more of the sensors based on one or more predetermined control profile(s). Various embodiments may advantageously dynamically (e.g., automatically) control physiological attributes (e.g., CSF attributes).

20 Claims, 4 Drawing Sheets

Related U.S. Application Data on Dec. 23, 2022, provisional application No. 63/477,162, filed on Dec. 23, 2022, provisional application No. 63/365,407, filed on May 26, 2022, provisional application No. 63/364,253, filed on May 5, 2022.

(56) References Cited

U.S. PATENT DOCUMENTS

| | | | | |
|---|---|---|---|---|
| 7,618,391 | B2 | 11/2009 | Madsen et al. | |
| 8,333,728 | B2 | 12/2012 | Bertrand et al. | |
| 8,870,787 | B2 | 10/2014 | Yadav et al. | |
| 8,992,456 | B1 | 3/2015 | Powell | |
| 9,072,865 | B2 | 7/2015 | Negre et al. | |
| 9,138,568 | B2 | 9/2015 | Swoboda et al. | |
| 10,272,188 | B1 | 4/2019 | Geiger et al. | |
| 10,695,484 | B1 | 6/2020 | Radojicic | |
| 11,247,030 | B2 | 2/2022 | Browd et al. | |
| 11,458,249 | B2 | 10/2022 | Morse et al. | |
| 2003/0032915 | A1 * | 2/2003 | Saul | A61B 5/031 604/9 |
| 2003/0163079 | A1 * | 8/2003 | Burnett | A61M 27/002 604/9 |
| 2004/0147871 | A1 * | 7/2004 | Burnett | A61M 39/24 604/9 |
| 2005/0277865 | A1 * | 12/2005 | Gharib | A61M 5/14276 604/9 |
| 2009/0005720 | A1 * | 1/2009 | Ludin | A61M 27/006 604/9 |
| 2009/0131850 | A1 | 5/2009 | Geiger | |
| 2009/0177279 | A1 | 7/2009 | Luciano et al. | |
| 2010/0130884 | A1 | 5/2010 | Linninger | |
| 2011/0004158 | A1 | 1/2011 | Luciano et al. | |
| 2011/0137182 | A1 | 6/2011 | Bellezza et al. | |
| 2012/0238936 | A1 * | 9/2012 | Hyde | A61B 5/1459 604/8 |
| 2013/0197422 | A1 * | 8/2013 | Browd | A61B 5/031 604/9 |
| 2014/0207045 | A1 | 7/2014 | Anand et al. | |
| 2014/0288459 | A1 | 9/2014 | Yadav et al. | |
| 2015/0112211 | A1 | 4/2015 | Purdy | |
| 2016/0331897 | A1 | 11/2016 | Anand et al. | |
| 2016/0331949 | A1 * | 11/2016 | Lutz | A61M 27/006 |
| 2016/0339216 | A1 | 11/2016 | Lenihan et al. | |
| 2017/0013622 | A1 | 1/2017 | Taylor | |
| 2017/0095649 | A1 | 4/2017 | Vase et al. | |
| 2017/0203084 | A1 | 7/2017 | Lad et al. | |
| 2017/0209056 | A1 | 7/2017 | Browd et al. | |
| 2018/0256911 | A1 | 9/2018 | Funane et al. | |
| 2020/0001059 | A1 | 1/2020 | Campbell et al. | |
| 2020/0046953 | A1 | 2/2020 | Vase | |
| 2020/0275948 | A1 | 9/2020 | Anand et al. | |
| 2021/0052811 | A1 | 2/2021 | Wostyn | |
| 2021/0052866 | A1 | 2/2021 | Roberts et al. | |
| 2021/0379344 | A1 * | 12/2021 | Hakim | A61M 27/006 |
| 2022/0105322 | A1 | 4/2022 | Riccardi et al. | |
| 2022/0265974 | A1 | 8/2022 | Saul et al. | |
| 2022/0361764 | A1 | 11/2022 | Sutin et al. | |
| 2023/0132409 | A1 * | 5/2023 | Morse | A61B 5/14532 604/9 |
| 2023/0363711 | A1 * | 11/2023 | Theodore | A61B 5/0031 |

FOREIGN PATENT DOCUMENTS

| | | | | |
|---|---|---|---|---|
| WO | 2010112555 | A1 | 10/2010 | |
| WO | 2011114260 | A1 | 9/2011 | |
| WO | 2022/016072 | * | 1/2022 | G01F 1/20 |
| WO | 2022055806 | A1 | 3/2022 | |

OTHER PUBLICATIONS

Guy, et al, CPAP pressure and flow data at 2 positive pressure levels and multiple controlled breathing rates from a trial of 30 adults, accessed Jan. 2, 2023,<https://bmcresnotes.biomedcentral.com/articles/10.1186/s13104-022-06133-w>.

Hamilton, R., Using Multi-Modality Measurements to Investigate Intracranial Pressure Waveform Morphology in Patients with Normal Pressure Hydrocephalus, 2014, retrieved from the internet, <https://escholarship.org/uc/item/6j98v27r>.

Irras, Active Fluid Exchange, accessed Apr. 13, 2023, <https://irras.com/product/proprietary-active-fluid-exchange/>.

Irras, Hummingbird Quad ICP Monitoring with Drainage Placement Instructions, accessed Apr. 13, 2013, <https://irras.com/wp-content/uploads/2020/08/IR-4984-H610-insertion-guide-poster-horizontal-v6.pdf>.

Irras, Hummingbird Quad ICP Monitoring with Drainage, accessed Apr. 13, 2023, <https:/irras.com/product/hummingbird/hummingbird-quad-icp-monitoring-with-drainage/>.

Irras, Introducing Hummingbird, accessed Apr. 13, 2023, <https://irras.com/product/hummingbird/>.

Irras, Introducing IRRAflow®, accessed Apr. 13, 2023, <https://irras.com/product/introducing-irraflow/>.

PX-Medical, How we work and the technology we use, accessed May 18, 2022, <https://www.px-medical.com/en/technology>.

Yiallourou, et al, Continuous positive airway pressure alters cranial blood flow and cerebrospinal fluid dynamics at the craniovertebral junction, Jun. 13, 2015, 8 pages.

* cited by examiner

DYNAMICALLY CONTROLLED CEREBROSPINAL FLUID SHUNT

CROSS-REFERENCE TO RELATED APPLICATIONS

This application claims the benefit of each of:

U.S. Application Ser. No. 63/364,253, titled "SHUNT TECHNOLOGY AND THE POTENTIAL FOR A SMART SHUNT," filed by Samuel Robert Browd on May 5, 2022;

U.S. Application Ser. No. 63/365,407, titled "Distributed Sensing and Control of Cerebrospinal Fluid," filed by Samuel Robert Browd, et al., on May 26, 2022;

U.S. Application Ser. No. 63/477,158, titled "Central Nervous System Monitoring and Intervention," filed by Samuel Robert Browd, et al., on Dec. 23, 2022;

U.S. Application Ser. No. 63/477,162, titled "Cerebrospinal Fluid Polarization," filed by Samuel Robert Browd, et al., on Dec. 23, 2022;

U.S. Application Ser. No. 63/488,412, titled "Dynamic Shunt Systems," filed by Samuel Robert Browd, et al., on Mar. 3, 2023.

This application incorporates the entire contents of the foregoing application(s) herein by reference.

TECHNICAL FIELD

Various embodiments relate generally to body fluid shunts.

BACKGROUND

Hydrocephalus is a condition in which an excess of cerebrospinal fluid (CSF) builds up in the ventricles within the brain. This increases the size and puts pressure on the ventricles, which can damage brain tissue and cause a variety of problems with brain function. CSF supports normal brain function by, by way of example and not limitation, keeping the brain buoyant in the skull, cushioning the brain to prevent injury, removing waste products, and maintaining a consistent pressure level within the brain. Hydrocephalus may, for example, occur when there is an imbalance in how much CSF is produced versus how much is absorbed into the bloodstream.

Although hydrocephalus can develop at any stage of life, it may, for example, be most prevalent in infants and adults over 60 years of age. Congenital hydrocephalus may, for example, be present at or shortly after birth due, by way of example and not limitation, to abnormal development of the central nervous system, complications of premature birth, and/or infections within the uterus during pregnancy. Hydrocephalus can, for example, develop at any age as a result of traumatic brain injury, haemorrhage, stroke, brain or spinal cord tumours, or infections such as meningitis or mumps.

SUMMARY

Apparatus and associated methods relate to smart shunt systems. In an illustrative example, a cerebrospinal fluid (CSF) shunt system includes an interface module and conduit(s) configured to provide selective fluid communication between a brain ventricle(s) and at least one reservoir. The interface module may be operably coupled to one or more control module(s). The control module(s) may, for example, be operably coupled to one or more actuator(s) and/or sensor(s) (e.g., in the interface module(s), external to the interface module(s)). The control module(s) may, for example, selectively operate one or more of the actuator(s) as a function of input received from one or more of the sensors based on one or more predetermined control profile(s). Various embodiments may advantageously dynamically (e.g., automatically) control physiological attributes (e.g., CSF attributes).

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, to help introduce discussion of various embodiments, a smart shunt system 110 is introduced with reference to FIG. 1. Second, that introduction leads into a description with reference to FIG. 2 of some exemplary embodiments of smart shunt systems in connection with various combinations of actuators and/or sensors, such as with respect to illustrative applications. Third, with reference to FIG. 3, embodiments of a smart shunt system provided with an interface between one or more shunt control modules and one or more shunt interface modules are described. Fourth, with reference to FIG. 4, the discussion turns to exemplary embodiments that illustrate an exemplary physiological shunt backflush generation system (PSBG). Finally, the document discusses further embodiments, exemplary applications and aspects relating to shunts in general and cerebrospinal shunts (e.g., dynamically controlled 'smart' shunts) in particular.

Figure 1:
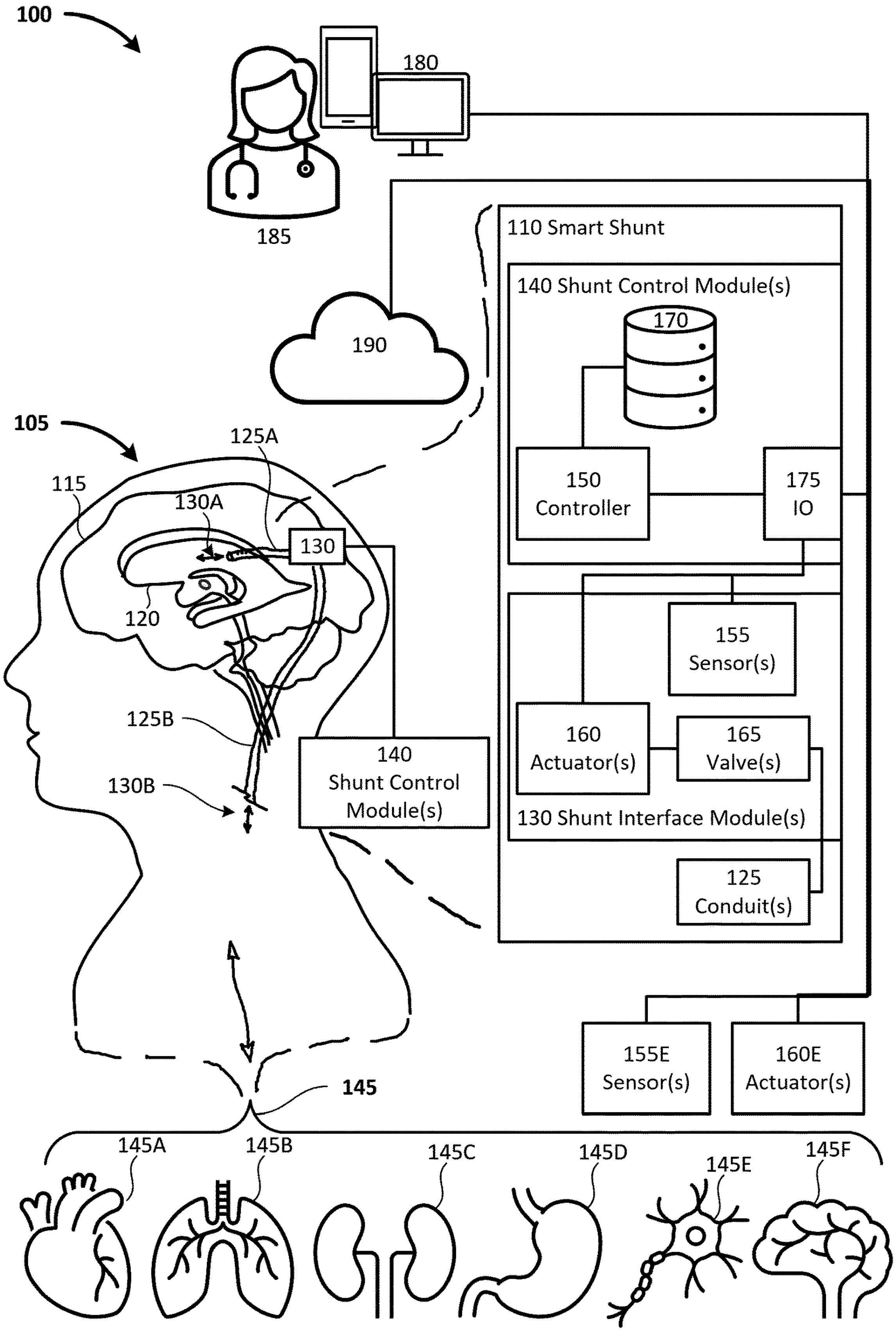
FIG. 1 depicts an exemplary smart shunt employed in an illustrative use-case scenario.

FIG. 1 depicts an exemplary smart shunt employed in an illustrative use-case scenario. In an illustrative smart shunt use case 100, a patient 105 is provided with a smart shunt 110. The smart shunt system 110 is embedded, in this example, in a ventricle 120 of a brain 115 of the patient 105. The smart shunt system 110 includes conduits 125 in fluid communication with at least one shunt interface module 130. As depicted, a first conduit 125A (e.g., a double lumen proximal catheter) is configured to provide fluid communication 130A between the depicted shunt interface module 130 and the ventricle 120. A second conduit 125B (e.g., a double lumen distal catheter) is in fluid communication 130B with one or more reservoirs and/or conduits (e.g., body cavities, naturally occurring physiological systems and/or conduits, implanted reservoirs and/or conduits, external reservoirs and/or conduits).

In the depicted example, the second conduit 125B may, for example, be in operable communication (e.g., fluid communication, electrical communication, mechanical communication, optical communication) with one or more physiological systems 145. In the depicted example, the physiological systems 145 may, for example, include one or more components of the cardiovascular system 145A. The physiological systems 145 may, for example, include one or more components of the pulmonary system 145B. The physiological systems 145 may, for example, include one or more components of the renal system 145C. The physiological systems 145 may, for example, include one or more components of the gastrointestinal system 145D. The physiological systems 145 may, for example, include one or more components of the peripheral nervous system 145E. The physiological systems 145 may, for example, include one or more components of the central nervous system 145F.

As depicted, one or more shunt interface modules 130 is operably coupled to (e.g., fluid communication, electrical communication, mechanical communication, optical communication, directly coupled to, integrated with) one or more shunt control modules 140. In this example, the shunt control module 140 includes a controller 150. The controller 150 may, by way of example and not limitation, include one or more of: a processor, memory module (e.g., random-access memory), and/or storage (e.g., non-volatile memory).

The shunt interface module 130 includes, in this depicted example, one or more sensors 155. The sensors 155 may, for example, monitor one or more of the physiological systems 145.

The shunt interface module 130 includes, in this example, one or more actuators 160. For example, as depicted, one or more of the actuators 160 are coupled to one or more corresponding valves 165. Valves 165 may, for example, selectively control fluid communication into, out of, and/or through one or more of the conduits 125 (e.g., first conduit 125A, second conduit 125B). One or more of the actuators 160 may, for example, be configured to affect one or more of the physiological systems 145. For example, the controller 150 may operate the actuators 160 according to predetermined control profiles 170 as a function of input from sensors 155.

In the depicted example, one or more of the sensors 155 are internal (e.g., integrated into) to one or more corresponding shunt interface modules 130. As shown, one or more of the shunt control modules 140 is connected to one or more external sensors 155E.

In the depicted example, one or more of the actuators 160 are internal (e.g., integrated into) to one or more corresponding shunt interface modules 130. As shown, one or more of the shunt control modules 140 is connected to one or more external actuators 160E.

In this example, the shunt control module 140 is coupled to the shunt interface module 130 via an input/output module (an IO module 175). In some examples, the IO module 175 may receive and/or transmit electrical signals (e.g., wired, wirelessly). In some examples, the IO module 175 may receive and/or transmit optical signals (e.g., 'wired', wirelessly). In some examples, the IO module 175 may receive and/or transmit mechanical signals (e.g., pressure, force, displacement).

The controller 150 of a shunt control module 140 may, as depicted, in operable communication with one or more external interfaces and/or control systems via the 10 module 175. In this depicted example, the shunt control module 140 is in operable communication with a display and/or control system 180. For example, an operator 185 (e.g., physician) may visualize data received from the smart shunt system 110 (e.g., parameters generated in response to sensors 155, control options available). The operator 185 may, for example, input commands (e.g., enable the smart shunt system 110, disable the smart shunt system 110; operate actuators 160; modify, activate, remove, create, and/or upload predetermined control profiles 170) to the smart shunt system 110.

As shown, in this example the shunt control module 140 is in operable communication with a cloud system 190. For example, the cloud system 190 may store and/or process data received from the smart shunt system 110. In some examples, the cloud system 190 may input commands and/or data to the smart shunt system 110. In some examples, the cloud system 190 may interact (e.g., receive data from, transmit data to) one or more control systems 180. For example, the cloud system 190 may generate graphical user interface(s) for display to an operator 185 as a function, for example, of data received from the smart shunt system 110.

Various embodiments advantageously provide dynamic control of cerebrospinal fluid (CSF) attributes (e.g., concentration, pressure, volume, flow) based on one or more predetermined control profiles and/or one or more physiological parameters.

For example, some embodiments may advantageously be configured as disclosed at least with reference to U.S. Application Ser. No. 63/364,253, titled "SHUNT TECHNOLOGY AND THE POTENTIAL FOR A SMART SHUNT," filed by Samuel Robert Browd on May 5, 2022, the entire contents of which are incorporated herein by reference.

Some embodiments may, for example, be configured as disclosed at least with reference to Appendix A of U.S. Application Ser. No. 63/488,412, titled "Dynamic Shunt Systems," filed by Samuel Robert Browd, et al., on Mar. 3, 2023, the entire contents of which are incorporated herein by reference.

For example, cerebrospinal fluid mechanics (e.g., flow, volume pressure) may be dynamically controlled via the actuators 160 based on data received from the sensors 155 and/or the operator 185, and/or based on one or more of the predetermined control profiles 170. As an illustrative example, valve(s) 165 may be selectively operated based on physiological parameters (e.g., intracranial pressure, heart rate, CSF pulsatility, intraventricular pressure). As an illustrative example, some embodiments may be implemented such as disclosed at least with reference to FIGS. 1-5 of U.S. Application Ser. No. 63/365,407, titled "Distributed Sensing and Control of Cerebrospinal Fluid," filed by Samuel Robert Browd, et al., on May 26, 2022, the entire contents of which are incorporated herein by reference.

As an illustrative example, CSF composition may be dynamically controlled via the actuators 160 based on data received from the sensors 155 and/or the operator 185, and/or based on one or more of the predetermined control profiles 170. For example, CSF may be filtered, denatured, and/or provided with additives based on predetermined (e.g., statically, dynamically) CSF composition criterion. For example, some embodiments may be implemented such as disclosed at least with reference to FIGS. 6-8 of U.S. Application Ser. No. 63/365,407, titled "Distributed Sensing and Control of Cerebrospinal Fluid," filed by Samuel Robert Browd, et al., on May 26, 2022, the entire contents of which are incorporated herein by reference.

As an illustrative example, CSF attributes may be selectively altered via actuators 160 as a function of attributes of one or more of the physiological systems 145 as determined by sensors 155 and based on operator 185 input and/or predetermined control profiles 170. For example, some embodiments may be implemented such as disclosed at least with reference to FIG. 9 of U.S. Application Ser. No. 63/365,407, titled "Distributed Sensing and Control of Cerebrospinal Fluid," filed by Samuel Robert Browd, et al., on May 26, 2022, the entire contents of which are incorporated herein by reference.

As an illustrative example, one or more of the physiological systems 145 may be selectively altered via actuators 160 as a function of CSF attributes determined by sensors 155 based on operator 185 input and/or predetermined control profiles 170. For example, some embodiments may be implemented such as disclosed at least with reference to FIG. 9 of U.S. Application Ser. No. 63/365,407, titled "Distributed Sensing and Control of Cerebrospinal Fluid," filed by Samuel Robert Browd, et al., on May 26, 2022, the entire contents of which are incorporated herein by reference.

Figure 2:
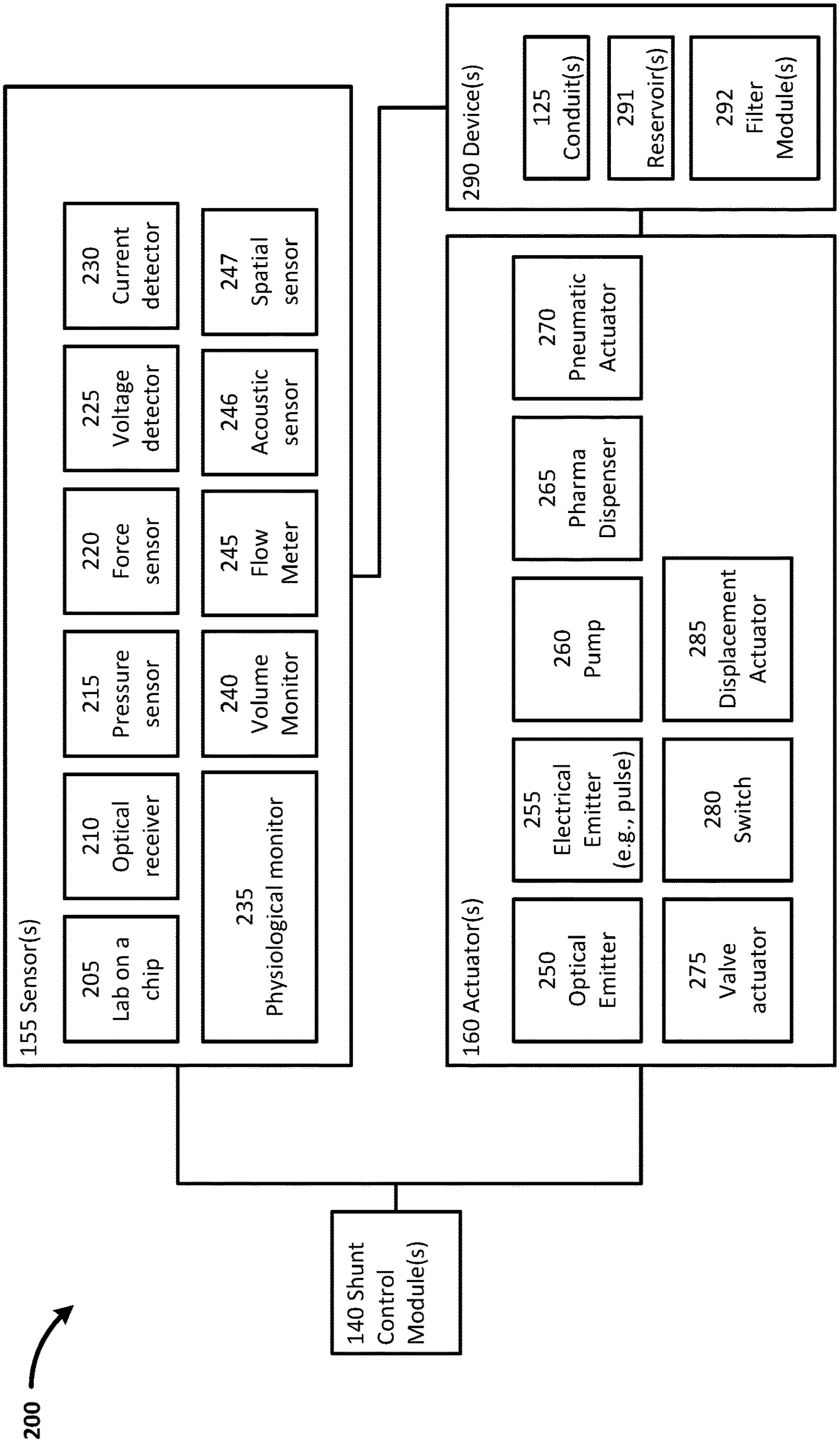
FIG. 2 is a block diagram depicting illustrative sensors and actuators connected to an exemplary smart shunt control module(s).

FIG. 2 is a block diagram depicting illustrative sensors and actuators connected to an exemplary smart shunt control module(s). In this example the shunt control module 140 is coupled to one or more sensors 155. As depicted, the sensors 155 may include a lab on a chip 205. Lab on a chip 205 may, for example, be configured to measure the presence of one or more analytes. For example, the lab on a chip 205 may detect the presence and/or other attribute (e.g., concentration, volume, flow) of one or more analytes in a physiological component (for example by fluid, tissue).

As depicted, the sensors 155 may include an optical receiver 210. The optical receiver 210 may, for example, transduce light (e.g., visible, infrared, ultraviolet). For example the optical receiver 210 may include a camera. The optical receiver 210 may include, for example, a photodetector. The optical receiver 210 may, for example, be configured to detect time of day (e.g., based on light presence, based on light frequency, based on light-colored temperature). The optical receiver 210 may, for example, be configured to measure ambient light impinging an external bodily surface (e.g., eyes, skin). The optical receiver 210 may, for example, be configured to detect harmful electromagnetic waves (e.g., ultraviolet light).

As depicted, the sensors 155 may, for example, include a pressure sensor 215. A pressure sensor 215 may, for example, be configured to detect intracranial pressure (ICP). Pressure sensor 215 may, for example, be configured to detect blood pressure. The pressure sensor 215 may, for example, be configured to detect pressure within a lumen of a fluid conduit (e.g., CSF pressure, air pressure). The pressure sensor 215 may, for example, be configured to detect transient pressure changes. For example, the pressure sensor 215 may be configured to measure pressure changes relative to a floating baseline. In some examples, the pressure sensor 215 may be configured to be calibrated in vivo against known changes (e.g., volume changes, physiological changes).

For example, some embodiments may, be configured as disclosed at least with reference to FIGS. 1-27 of U.S. Application Ser. No. 63/488,412, titled "Dynamic Shunt Systems," filed by Samuel Robert Browd, et al., on Mar. 3, 2023, the entire contents of which are incorporated herein by reference.

As depicted, the sensors 155 may, for example, include a force sensor 220. The force sensor 220 may, for example, be configured to detect touch. The force sensor 220 may, for example, be configured to detect force correlating to a pressure.

As depicted, the sensors 155 may include a voltage detector 225. The voltage detector 225 may, for example, be configured to detect electric potential in the CSF. The voltage detector 225 may, for example, be configured to detect electric potential of neural tissue. The voltage detector 225 may, for example, be configured to detect brain activity (e.g., electroencephalogram). The voltage detector 225 may, for example, be configured to detect cardiac activity (e.g., electrocardiogram).

As depicted, the sensors 155 may include a current detector 230.

As depicted, the sensors 155 include a physiological monitor 235, such as, for example, a system configured to detect one or more physiological attributes. By way of example and not limitation, a physiological monitor 235 may include a heart rate monitor. A physiological monitor 235 may, for example, include a blood pressure monitor. A physiological monitor 235 may, for example, include a pulse oximeter.

As depicted, the sensors 155 include a volume monitor 240. For example, volume monitor may detect volume and/or mass (e.g., of fluid, of a solid(s)). By way of example and not limitation, a volume monitor may measure volume as a function of electrical capacitance in a cavity.

As depicted, the sensors 155 may include a flow meter 245. A flow meter 245 may, for example, be configured to measure CSF flow rate. A flow meter 245 may, for example, be configured to measure flow rate of a fluid through a conduit (e.g., through a valve, through a catheter). A flow meter 245 may, for example, be configured to measure blood flow. A flow meter 245 may, for example, be configured to measure pulmonary capacity.

As depicted, the sensors 155 may include an acoustic sensor 246. The acoustic sensor 246 may, for example, detect pulmonary parameters (e.g., breath rate). The acoustic sensor 246 may, for example, detect cardiovascular parameters (e.g., heart rate). The acoustic sensor 246 may, for example, detect gastrointestinal parameters (e.g., gastric peristalsis).

As depicted, the sensors 155 may include a spatial sensor 247. The spatial sensor 247 may, for example, detect a position of the patient 105. A spatial sensor 247 may, for example, include a motion and/or orientation sensor. For example, the spatial sensor 247 may, for example, include a gyroscope.)

In this example the shunt control module 140 is coupled to one or more actuators 160. As depicted, the actuators 160 may include an optical emitter 250. For example, the optical emitter 250 may be configured to emit visible light. The optical emitter 250 may, for example, be configured to emit infrared light. The optical emitter 250 may, for example, be configured to emit ultraviolet light. As an illustrative example, the optical emitter 250 may be selectively operated to denature contaminant proteins (e.g., Alzheimer's contributory proteins in CSF, toxins, contaminants).

For example, in some implementations, the smart shunt system 110 may be configured to operate one or more optical emitter 250 such that target contaminants of the CSF are altered to initiate and/or enhance removal (e.g., artificial such as filtration, physiological such as through normal physiological processes).

In some implementations, for example, the optical emitter 250 may be selectively operated to induce photosensitive processes in the body of the patient 105 (e.g., autologous biochemical production and/or cascades).

As depicted, the actuators 160 may include an electrical emitter 255. For example, the electrical emitter 255 may be configured to emit a varying (e.g., pulsed) electrical current. In some examples, the electrical emitter 255 may be configured to emit a static electrical current. In some examples, the electrical matter to 55 may be configured to generate a target voltage (e.g., static, dynamic).

For example, some implementations may be configured such as disclosed at least with reference to paragraphs [0003-0053] of U.S. Application Ser. No. 63/477,162, titled "Cerebrospinal Fluid Polarization," filed by Samuel Robert Browd, et al., on Dec. 23, 2022, the entire contents of which are incorporated herein by reference.

As depicted, the actuators 160 may include pump 260. For example, pump 260 may be configured to move bodily fluid (e.g., CSF fluid, blood, discharge). In some implementations, a pump 260 may include a mechanical pump (e.g., peristaltic pump, diaphragm pump, auger pump, impeller pump). In some implementations, a pump 260 may include an electrically-powered pump. In some implementations, a pump 260 may include a chemically based pump (e.g., osmotic pump).

As depicted, the actuators 160 may include a pharmaceutical dispenser 265. For example, the pharmaceutical dispenser 265 may be configured to selectively dispense pharmaceutical and/or nutraceuticals compounds to the patient 105.

For example, the pharmaceutical dispenser 265 may be selectively operated as a function of CSF parameters. In some implementations, for example, the pharmaceutical dispenser 265 may be operated to selectively dispense additives into the CSF.

As depicted, the actuators 160 may include a pneumatic actuator 270. The pneumatic actuator 270 may, for example, be configured to apply a mechanical stimulus.

In some implementations by way of example and not limit limitation, the pneumatic actuator 270 may be configured to dispense an oxygen-rich supply to the patient 105.

As depicted, the actuators 160 may include a valve actuator 275. For example, the valve actuator 275 may be configured to operate a valve 165. In some examples, the valve actuator 275 may include a solenoid operated valve mechanism. In some examples the valve actuator 275 may include a linear actuator of a valve. In some examples, the valve actuator 275 may include a rotary actuator of a valve.

As depicted, the actuators 160 may include a switch 280. For example a switch 280 may be configured to selectively provide electrical current to a load.

As depicted, the actuators 160 may include a displacement actuator 285. For example, displacement actuator 285 may be configured as a pump (e.g., pump 260). In some embodiments, displacement actuator 285 may be configured to provide a baseline calibration reference. The displacement actuator 285 may, for example, include a self-powered (e.g., pneumatic, electric, hydraulic) displacement actuator.

In some implementations, for example, the displacement actuator 285 may include an externally powered displacement actuator (e.g., bulb, membrane, flexible fluid reservoir).

As depicted, one or more of the sensors 155 and/or the actuators 160 may be operably coupled to one or more controlled device 290. For example, an actuator 160 may be coupled to a conduit 125 (e.g., fluidly coupled). For example, a displacement actuator 285 may be configured to mechanically displace (e.g., 'squeeze') a flexible conduit 125 (e.g., to generate a pressure wave, to induce fluid flow). For example, a pump 260 may be fluidly coupled to displace fluid into a reservoir 291, such as through a conduit 125 and/or filter module(s) 292. A flow meter 245 may, for example, be configured to determine flow through a conduit 125 into and/or out of a filter module 292. An optical receiver 210 may, for example, be configured to detect optical attributes (e.g., turbidity) of CSF in a filter module 292.

Although various sensors and actuators are depicted, various embodiments may include some, all, or none of the depicted sensors and/or the depicted actuators.

In some implementations, for example, multiple shunt control modules 140 and/or multiple shunt interface module 130 may be spatially distributed along a smart shunt system 110. In some implementations, for example, a shunt control module 140 and/or shunt interface module 130 may be spatially distributed throughout and/or across (e.g., externally) a body of the patient 105.

For example, some implementations may include distributed sensing and/or control such as disclosed at least with reference to FIG. 1 of U.S. Application Ser. No. 63/477,158, titled "Central Nervous System Monitoring and Intervention," filed by Samuel Robert Browd, et al., on Dec. 23, 2022, the entire contents of which are incorporated herein by reference.

Some implementations may, for example, such as disclosed at least with reference to FIG. 1 of U.S. Application Ser. No. 63/477,158, titled "Central Nervous System Monitoring and Intervention," filed by Samuel Robert Browd, et al., on Dec. 23, 2022, the entire contents of which are incorporated herein by reference.

Figure 3:
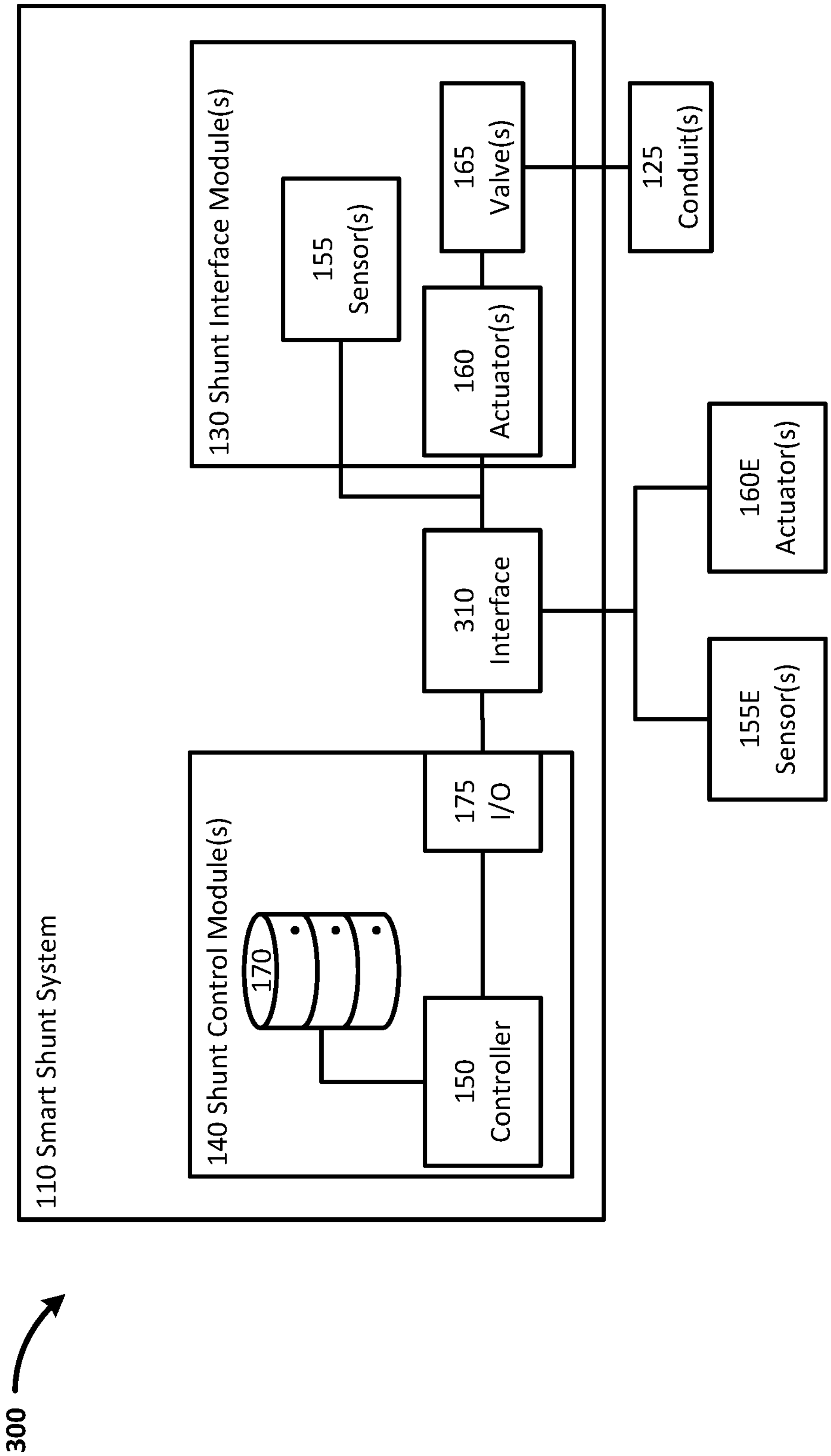
FIG. 3 is a block diagram depicting an embodiment of the exemplary smart shunt system including an interface.

FIG. 3 is a block diagram depicting an embodiment of the exemplary smart shunt system including an interface. in the depicted example, a shunt control module 140 and a shunt interface module 130 are connected via an interface 310. An interface 310 may, for example, be remote (e.g., in the cloud system 190).

In some implementations, for example, an interface 310 may, for example, be handheld. For example, an operator 185 may operate an interface 310 to read data (e.g., pressure, volume, concentration) corresponding to the shunt interface module 130. The interface 310 may, for example, have received (e.g., downloaded) control information (e.g., predetermined control profile 170) from the shunt control module 140. In some implementations, the interface 310 may, for example, be in communication with the shunt control module 140 (e.g., continuously, intermittently, periodically).

For example, the shunt control module 140 may be local on the interface 310.

In some implementations, the shunt control module 140 may be on the cloud system 190 and/or the control system 180.

In some implementations, a first shunt control module 140 may, for example, be coupled to (e.g., integrated with, plugged into) the shunt interface module 130. A second shunt control module 140 may, for example, be on the interface 310 and/or in communication (e.g., continuously, periodically, selectively) with the interface 310. The first shunt control module 140 may, for example, monitor and/or control the shunt interface module 130 based on instructions (e.g., a predetermined control profile 170) received from the second shunt control module 140 (e.g., via the interface 310).

In the depicted example, the interface 310 is further operably coupled to one or more external sensors 155E and/or one or more external actuators 160E. For example, the interface 310 may be coupled to a vital signs monitor. The interface 310 may, for example, be coupled to an insulin pump. The interface 310 may, for example, be coupled to an imaging device.

Figure 4:
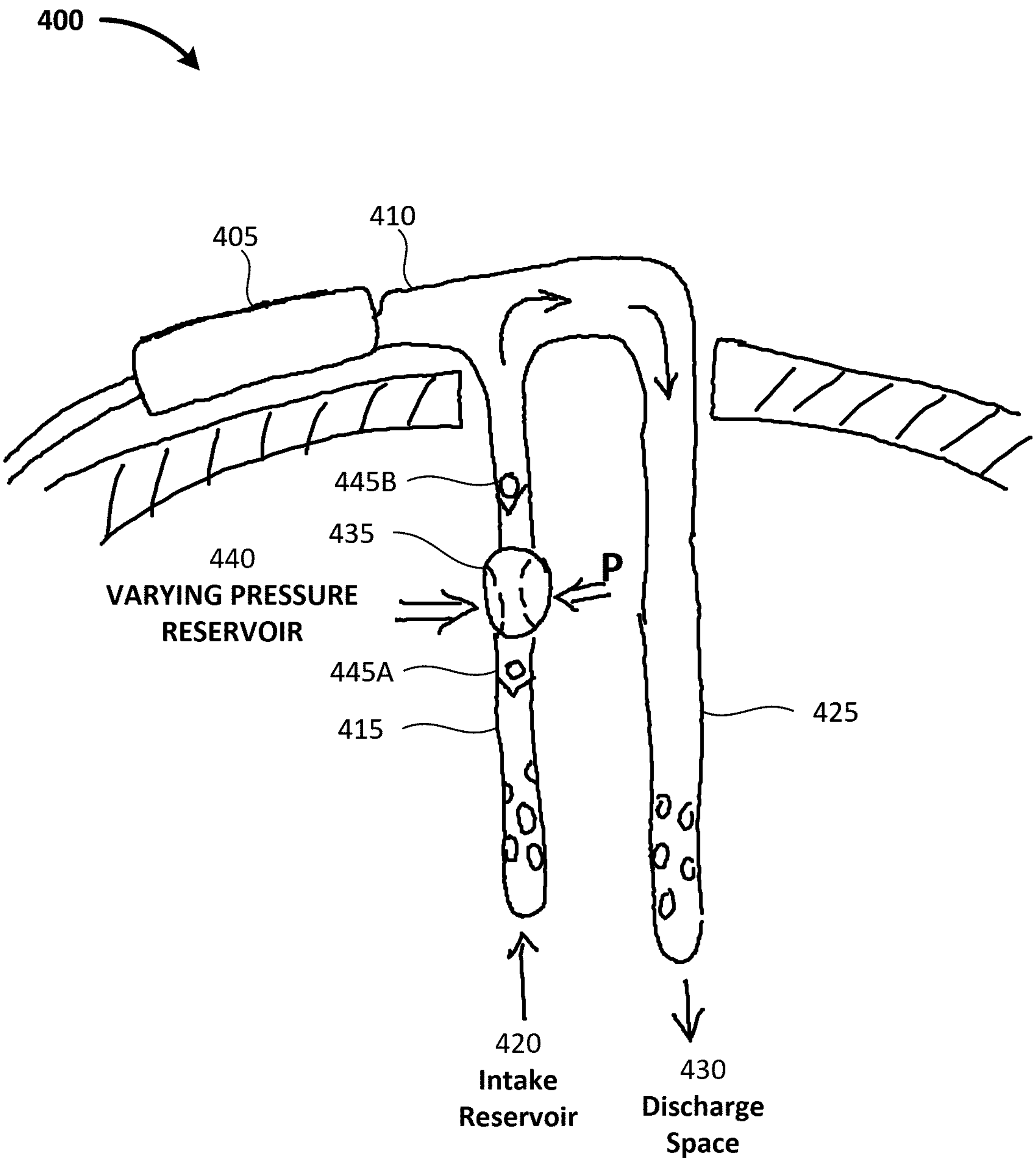
FIG. 4 is a schematic view of an exemplary physiological shunt backflush generation system (PSBG).

FIG. 4 is a schematic view of an exemplary physiological shunt backflush generation system (PSBG). In the depicted example, a shunt 405 (e.g., configured as part or all of a smart shunt system 110) is in fluid communication with a physiologically-flushed proximal catheter 410. The physiologically-flushed proximal catheter 410 includes a discharge catheter 425 and an intake catheter 415. The 415 is in fluid communication with an intake reservoir 420 (e.g., a ventricle 120). The discharge catheter 425 is in fluid communication with a discharge space 430 (e.g., a ventricle 120, a separate reservoir).

The physiologically-flushed proximal catheter 410 includes a physiologically-activated pump 435 (e.g., a reservoir with walls configured to be displaced under physiologically available pressures) in fluid communication with the intake catheter 415 and the discharge catheter 425. The physiologically-activated pump 435 is disposed in a varying pressure reservoir 440. The varying pressure reservoir 440 may, for example, include the ventricle 120. In some implementations, the varying pressure reservoir 440 may be separate from (e.g., independent of) the intake reservoir 420.

First valve 445A and second valve 445B are, in this example, disposed on either side of the 435. In some implementations, the valves 445 may, for example, be passive valves (e.g., check valves, umbrella valves). In some implementations, the valves 445 may, for example, be dynamically configured and/operated valves (e.g., by an actuator 160).

In response to a transient event (e.g., a transient pressure event, such as induced by a patient coughing, sneezing, bending over, blowing their nose, picking up an object, lying down, standing up), a pressure increase may be generated in the varying pressure reservoir 440. A pressure "P" in the varying pressure reservoir 440 may, for example, exceed an operation pressure of the physiologically-activated pump 435 such that the physiologically-activated pump 435 is operated (e.g., 'squeezed' as shown), inducing displacement of fluid from the physiologically-activated pump 435 to induce backflushing through the discharge catheter 425. For example, the discharge catheter 425 may normally be an intake conduit for discharge through the shunt 405 to relieve excess CSF from the ventricle 120.

In some implementations, for example, the intake catheter 415 and/or the discharge catheter 425 may be interchangeable. For example, the intake catheter 415 may operate as a discharge catheter using fluid received through the discharge catheter 425, such as to backflush the intake catheter 415.

Various embodiments may advantageously reduce or prevent obstruction of the intake catheter 415 and/or the discharge catheter 425.

For example, some embodiments may, be configured as disclosed at least with reference to FIGS. 28-32 of U.S. Application Ser. No. 63/488,412, titled "Dynamic Shunt Systems," filed by Samuel Robert Browd, et al., on Mar. 3, 2023, the entire contents of which are incorporated herein by reference.

Although various embodiments have been described with reference to the figures, other embodiments are possible.

Although an exemplary system has been described with reference to FIG. 1, other implementations may be deployed in other industrial, scientific, medical, commercial, and/or residential applications.

For example, some embodiments of smart shunts as disclosed herein may be configured as active implants. The implant may, for example, include a surgically advantageous form factor and/or location(s) (e.g., under a scalp).

Various embodiments may advantageously provide body driven backflushing.

Some embodiments may, for example, provide CSF shunt diagnostics. For example, some embodiments may include non-calibrated and/or drifting pressure sensor diagnostics.

Some embodiments may, for example, include non-fluid communicating recalibration.

For example, some embodiments may be configured as disclosed at least with reference to FIGS. 1-27 and Appendix A of U.S. Application Ser. No. 63/488,412, titled "Dynamic Shunt Systems," filed by Samuel Robert Browd, et al., on Mar. 3, 2023, the entire contents of which are incorporated herein by reference.

Some embodiments may, for example, provide therapeutics (e.g., actively controlled, CSF attribute-linked). For example, some embodiments may be configured to provide CSF composition therapy regulated by energy only (e.g., light).

Some embodiments may, for example, advantageously harvest energy (e.g., from the patient 105). As an illustrative example, dual lumen tubing may be configured for active backflushing and/or exchange, and/or for pressure control). For example, some embodiments may be configured such as disclosed at least with reference to U.S. Application Ser. No. 63/364,253, titled "SHUNT TECHNOLOGY AND THE POTENTIAL FOR A SMART SHUNT," filed by Samuel Robert Browd on May 5, 2022, the entire contents of which are incorporated herein by reference.

Some embodiments may, for example, be configured as an external ventricular drain (EVD).

Some embodiments may, for example, advantageously provide variable hole sizes in a proximal catheter. The variable hole sizes may, for example, advantageously provide a higher flow at a distal end.

Some embodiments may, for example, advantageously provide an external reader (e.g., interface 310). The external reader may, for example, transmitted power to an implanted device (e.g., shunt interface module 130, shunt control module 140).

Some embodiments may advantageously include implanted electronics and/or implanted power. Some embodiments may include an implanted control algorithm (e.g., in a shunt control module 140).

Some embodiments may, for example, advantageously reduce neurotoxins from CSF and/or control a composition of the CSF (e.g., compensating for a failed natural mechanism(s)). For example, some embodiments may advantageously remove and/or replace the CSF with another fluid. Some embodiments may, for example, advantageously filter the CSF. Some embodiments may, for example, advantageously introduce additives from reservoirs.

Some embodiments may, for example, advantageously be informed by a "lab-on-a-chip" module configured to measure target analytes in the CSF.

In some implementations, for example, CSF may be passed through a reservoir having an amyloid binding agent. The agent may, for example, bind to amyloids in the CSF. The agent may, for example, then be captured (e.g., by a gravity trap, by a magnetic field), thereby removing the amyloids from the CSF. Such implementations may, for example, advantageously be used to treat Alzheimer's.

Some embodiments may, for example, advantageously draw out and replace fluid (e.g., simultaneously) in a "push-pull" configuration.

Some embodiments may, for example, advantageously actively control pressure wave form in the brain.

Some embodiments may, for example, be provided with dual lumen tube, such as for fluid exchange Some embodiments may, for example, advantageously provide ion exchange and/or an electro osmotic pump for operating on the CSF.

Some embodiments may, for example, advantageously treat CSF (e.g., infection, contaminants) with a sanitizing module (e.g., UV-C light).

Some embodiments may, for example, advantageously provide a balloon (e.g., displacement actuator 285) in the ventricles to control and/or measure attributes within the ventricles (e.g., static, dynamic). For example, the balloon may be expanded to a known expansion, measure pressure change to measure compliance.

Some embodiments may, for example, advantageously be configured to collect debris, proteins, and/or other target composition(s). The collected composition(s) may, for example, be extracted periodically (e.g., from a collection reservoir). In some implementations, for example, the collected compositions may be processed (e.g., by denaturing proteins) before being disposed (e.g., pushed) back into the CSF.

Some embodiments may, for example, advantageously control pressure waveform with active input.

Some embodiments may, for example, advantageously provide light therapy for the brain.

As an illustrative example, some embodiments may include an implant. The implant may, for example, be configured to receive energy (e.g., transcutaneously) from an external device (e.g., mounted on a head band and/or 'cap', disposed in a pillow) worn by the patient. The implant may, for example, move CSF though a cleaning module. The implant may, for example, apply UV light to the CSF (e.g., to denature target proteins). In some implementations, for example, electric fields may be applied to isolate a first set of target proteins (e.g., harmful proteins) from a second set of target proteins (e.g., useful proteins).

Samples may, for example, be taken before and/or after processing. For example, the samples may be tested to determine efficacy and/or operating attributes of the system.

Some embodiments may, for example, be configured to introduce and/or remove a bolus of fluid. For example, the bolus may correspond to a known parameter (e.g., pressure, volume, flow, mass). The bolus removal and/or introduction may be used to calibrate a component (e.g., a sensor 155 such as a pressure sensor 215).

For example, some embodiments may be configured to calibrate corresponding to a bolus based on a relationship defined by the ideal gas law.

For example, some embodiments may be configured to calibrate corresponding to a bolus based on a relationship to fluid properties such as osmolality and/or pH.

Some embodiments may, for example, advantageously be configured for patients with diseases related to natural filtering and/or toxins, but who still have healthy natural control of CSF flow and/or ICP. As an illustrative example, an active filtering module (e.g., including a pump 260, including a filter module 292) may be inserted into the ventricle 120. In some implementations, for example, wires may lead to the filtering module. The filtering module may, for example, always have CSF flowing through it (e.g., which may advantageously reduce clogging). A battery connected to the filtering module may, for example, be periodically charged.

Some embodiments may, for example, advantageously push captured toxins or other compounds out (e.g., through a shunt system, such as including a conduit 125). For example, some embodiments may include a drain (e.g., for patients that need additional cleaning). Some embodiments may, for example, be coupled in fluid communication with existing drains for patients with shunts.

Some embodiments may, for example, concentrate target compounds (e.g., toxins) into a solution (e.g., a brine) and drain the solution (e.g., instead of CSF).

For example, some embodiments may advantageously amplify an amount of removal of the target compound(s) that occurs during natural flow of CSF.

Some embodiments may, for example, collect sterile fluid from the abdomen, filter to pure water, and pump into the brain.

Some embodiments may, for example, be in fluid communication with the patient's blood stream. Fluid from the blood stream may, for example, be filtered. Plasma and/or pure water filtered from the blood may be disposed into the brain.

Some embodiments may, for example, be configured to move CSF from the head to an abdominal module, clean it, then pump back to the head. Some embodiments may, for example, be configured to permit periodic exchange of a brine from the module via, for example, a self-healing septum.

Some embodiments may, for example, be configured to achieve regular flow (e.g., of CSF).

For example, some embodiments may be configured to use abdominal pressure events to push flow through the device (e.g., the smart shunt system 110). For example, energy may be collected (e.g., as disclosed at least with reference to FIG. 4) from an abdominal pressure event. The energy collected may, for example, be released over time (e.g., immediately, slowly), such as by operation of a piston.

Some embodiments may, for example, harvest unusual fluid motivation phenomena (e.g., chemically-induced flow, transient pressure events) to generate small (e.g., very small) pressures and/or small flow rates sufficient to drive flow through a smart shunt system 110. Such systems may, for example, advantageously reduce space and/or energy use, and/or may provide a more robust function.

Some embodiments may, for example, provide CSF composition therapy. For example, such embodiments may advantageously compensate for failed and/or overwhelmed natural CSF filtering mechanisms.

Some embodiments may, for example, advantageously use energy only to adjust CSF composition (e.g., light energy, electrical potential energy, chemical energy). For example, some embodiments may not use artificially generated mechanical stimuli.

Some embodiments may, for example, drain CSF residue (e.g., after filter) into the body.

Some embodiments may, for example, be configured to remove CSF residue from the body.

Some embodiments may, for example, introduce a binding agent into and/or in proximity to the CSF such that target compounds are captured as CSF and removed with the binding agent.

Some embodiments may, for example, provide drug injection into the CSF and/or combine CSF therapy with drug introduction into another portion of the patient's body. For example, CSF therapy may be combined with oral and/or nasal drug delivery.

In various embodiments, some bypass circuits implementations may be controlled in response to signals from analog or digital components, which may be discrete, integrated, or a combination of each. Some embodiments may include programmed, programmable devices, or some combination thereof (e.g., PLAs, PLDs, ASICs, microcontroller, microprocessor), and may include one or more data stores (e.g., cell, register, block, page) that provide single or multi-level digital data storage capability, and which may be volatile, non-volatile, or some combination thereof. Some control functions may be implemented in hardware, software, firmware, or a combination of any of them.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an example of a system, which may be portable, has been described with reference to the above figures, other implementations may be deployed in other processing applications, such as desktop and networked environments.

Temporary auxiliary energy inputs may be received, for example, from chargeable or single use batteries, which may enable use in portable or remote applications. Some embodiments may operate with other DC voltage sources, such as a 1.5V or 9V (nominal) battery, for example. Alternating current (AC) inputs, which may be provided, for example from a 50/60 Hz power port, or from a portable electric generator, may be received via a rectifier and appropriate scaling. Provision for AC (e.g., sine wave, square wave, triangular wave) inputs may include a line frequency transformer to provide voltage step-up, voltage step-down, and/or isolation.

Although particular features of an architecture have been described, other features may be incorporated to improve performance. For example, caching (e.g., L1, L2, . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades), and the like. One or more communication interfaces may be provided in support of data storage and related operations.

Some systems may be implemented as a computer system that can be used with various implementations. For example, various implementations may include digital circuitry, analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. Various embodiments may be implemented in a computer system that includes a graphical user interface and/or an Internet browser. To provide for interaction with a user, some implementations may be implemented on a computer having a display device. The display device may, for example, include an LED (light-emitting diode) display. In some implementations, a display device may, for example, include a CRT (cathode ray tube). In some implementations, a display device may include, for example, an LCD (liquid crystal display). A display device (e.g., monitor) may, for example, be used for displaying information to the user. Some implementations may, for example, include a keyboard and/or pointing device (e.g., mouse, trackpad, trackball, joystick), such as by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/ or optical networks, the computers and networks forming the Internet, or some combination thereof. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11a/b/g, Wi-Fi, Ethernet, IrDA, FDDI (fiber distributed data interface), token-ring networks, multiplexing techniques based on frequency, time, or code division, or some combination thereof. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

Various examples of modules may be implemented using circuitry, including various electronic hardware. By way of example and not limitation, the hardware may include transistors, resistors, capacitors, switches, integrated circuits, other modules, or some combination thereof. In various examples, the modules may include analog logic, digital logic, discrete components, traces and/or memory circuits fabricated on a silicon substrate including various integrated circuits (e.g., FPGAs, ASICs), or some combination thereof. In some embodiments, the module(s) may involve execution of preprogrammed instructions, software executed by a processor, or some combination thereof. For example, various modules may involve both hardware and software.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A cerebrospinal fluid shunt comprising:

a proximal conduit configured to be implanted in fluid communication at a distal end with a brain ventricle of a patient;

a distal conduit configured to be implanted in fluid communication at a distal end with a reservoir;

a dynamically controlled valve module operably coupled to the proximal end of the proximal conduit and the proximal end of the distal conduit, the dynamically controlled valve module selectively operable to permit fluid communication between the distal conduit and the proximal conduit;

a pressure sensor configured to detect a transient pressure in the ventricle;

one or more sensors operatively coupled to the proximal conduit and configured to collect physiological signals from the patient;

one or more actuators operatively coupled to the proximal conduit and configured to perform actions based on control signals; and, a control module in operable communication with the dynamically controlled valve, the pressure sensor, the one or more sensors, and the one or more actuators, such that, in response to detecting a transient pressure event in the ventricle that meets at least one criterion determined as a function of a predetermined control profile, then the dynamically controlled valve is operated to provide a corresponding predetermined flow profile between the distal conduit and the proximal conduit, wherein the control module:

analyzes a pressure waveform generated by the pressure sensor to detect and characterize transient pressure events;

extracts diagnostic information from the transient pressure events;

adjusts operation of the dynamically controlled valve based on the diagnostic information;

collects multiple physiological signals from the one or more sensors;

operates the one or more actuators based on the physiological signals from the one or more sensors; and, stores the physiological signals from the one or more sensors.

2. The cerebrospinal fluid shunt of claim 1, wherein:

the transient pressure event comprises a transient pressure maximum generated by bodily motion of the patient, the at least one criterion comprises a pressure change over time threshold, and the dynamically controlled valve is operated to at least partially interrupt flow from the ventricle into the reservoir.

3. The cerebrospinal fluid shunt of claim 1, wherein the dynamically controlled valve module comprises a plurality of valves.

4. The cerebrospinal fluid shunt of claim 1, wherein the reservoir comprises a body cavity.

5. The cerebrospinal fluid shunt of claim 1, further comprising a backflush reservoir, wherein:

the dynamically controlled valve module is further in selective fluid communication with the backflush reservoir; and, the predetermined flow profile is further configured such that the dynamically controlled valve module is operated to cause fluid from the backflush reservoir to be discharged through at least the proximal end of the proximal conduit in response to the transient pressure event.

6. The cerebrospinal fluid shunt of claim 1, wherein the one or more sensors further comprise a volume monitor.

7. A cerebrospinal fluid shunt comprising:

a proximal conduit configured to be implanted in fluid communication at a distal end with a brain ventricle of a patient;

a distal conduit configured to be implanted in fluid communication at a distal end with a reservoir;

a dynamically controlled valve module operably coupled to the proximal end of the proximal conduit and the proximal end of the distal conduit, the dynamically controlled valve module selectively operable to permit fluid communication between the distal conduit and the proximal conduit;

a pressure sensor configured to detect a transient pressure in the ventricle;

one or more sensors operatively coupled to the proximal conduit and configured to collect physiological signals from the patient;

one or more actuators operatively coupled to the proximal conduit and configured to perform actions based on control signals; and, a control module in operable communication with the dynamically controlled valve, the pressure sensor, the one or more sensors, and the one or more actuators, such that, in response to detecting a transient pressure event in the ventricle that meets at least one criterion determined as a function of a predetermined control profile, then the dynamically controlled valve is operated to provide a corresponding predetermined flow profile between the distal conduit and the proximal conduit, wherein the control module:

analyzes a pressure waveform generated by the pressure sensor to detect and characterize transient pressure events;

extracts diagnostic information from the transient pressure events;

adjusts operation of the dynamically controlled valve based on the diagnostic information;

collects multiple physiological signals from the one or more sensors;

operates the one or more actuators based on the physiological signals from the one or more sensors; and, stores the physiological signals from the one or more sensors; and, an input/output module in operable communication with the control module, wherein the input/output module is configured to exchange signals with an external interface device.

8. The cerebrospinal fluid shunt of claim 7, wherein the one or more sensors further comprise an acoustic sensor.

9. The cerebrospinal fluid shunt of claim 7, wherein the one or more sensors further comprise a force sensor.

10. The cerebrospinal fluid shunt of claim 7, wherein the one or more sensors further comprise a spatial sensor.

11. The cerebrospinal fluid shunt of claim 7, wherein the one or more actuators further comprise a valve actuator.

12. The cerebrospinal fluid shunt of claim 7, wherein the one or more actuators further comprise a pump.

13. The cerebrospinal fluid shunt of claim 7, wherein the one or more actuators further comprise an optical emitter.

14. A cerebrospinal fluid shunt comprising:

a proximal conduit configured to be implanted in fluid communication at a distal end with a brain ventricle of a patient;

a distal conduit configured to be implanted in fluid communication at a distal end with a reservoir;

a dynamically controlled valve module operably coupled to the proximal end of the proximal conduit and the proximal end of the distal conduit, the dynamically controlled valve module selectively operable to permit fluid communication between the distal conduit and the proximal conduit;

a pressure sensor configured to detect a transient pressure in the ventricle;

one or more sensors operatively coupled to the proximal conduit and configured to collect physiological signals from the patient;

one or more actuators operatively coupled to the proximal conduit and configured to perform actions based on control signals; and, a control module in operable communication with the dynamically controlled valve, the pressure sensor, the one or more sensors, and the one or more actuators, such that, in response to detecting a transient pressure event in the ventricle that meets at least one criterion determined as a function of a predetermined control profile, then the dynamically controlled valve is operated to provide a corresponding predetermined flow profile between the distal conduit and the proximal conduit, wherein the control module:

analyzes a pressure waveform generated by the pressure sensor to detect and characterize transient pressure events;

extracts diagnostic information from the transient pressure events;

adjusts operation of the dynamically controlled valve based on the diagnostic information;

collects multiple physiological signals from the one or more sensors;

operates the one or more actuators based on the physiological signals from the one or more sensors; and, stores the physiological signals from the one or more sensors; and a filter module disposed in fluid communication with the proximal conduit and the distal conduit, such that the filter module is configured to filter cerebrospinal fluid as the cerebrospinal fluid flows therethrough.

15. The cerebrospinal fluid shunt of claim 14, wherein the one or more actuators further comprise an electrical emitter.

16. The cerebrospinal fluid shunt of claim 14, wherein the one or more actuators further comprise a pharmaceutical dispenser.

17. The cerebrospinal fluid shunt of claim 14, wherein the one or more actuators further comprise a pneumatic actuator.

18. The cerebrospinal fluid shunt of claim 14, wherein the one or more actuators further comprise a displacement actuator.

19. The cerebrospinal fluid shunt of claim 14, wherein the one or more actuators further comprise a switch.

20. The cerebrospinal fluid shunt of claim 14, wherein the one or more sensors further comprise a lab-on-a-chip sensor.

* * * * *